(12) United States Patent
Biedermann et al.

(10) Patent No.: US 9,730,745 B2
(45) Date of Patent: Aug. 15, 2017

(54) BONE ANCHOR WITH PLUG MEMBER AND TOOL FOR INSERTING THE PLUG MEMBER INTO THE BONE ANCHOR

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/991,822

(22) Filed: Jan. 8, 2016

(65) Prior Publication Data
US 2016/0220292 A1 Aug. 4, 2016

Related U.S. Application Data

(63) Continuation of application No. 14/188,391, filed on Feb. 24, 2014, now Pat. No. 9,265,539, which is a (Continued)

(30) Foreign Application Priority Data

Jul. 1, 2008 (EP) .................................... 08011874

(51) Int. Cl.
*A61B 17/70* (2006.01)
*A61B 17/88* (2006.01)
*A61B 17/86* (2006.01)

(52) U.S. Cl.
CPC ...... *A61B 17/8811* (2013.01); *A61B 17/7037* (2013.01); *A61B 17/7098* (2013.01);
(Continued)

(58) Field of Classification Search
CPC .................................................. A61B 17/7098
See application file for complete search history.

(56) References Cited

U.S. PATENT DOCUMENTS 4,523,910 A 6/1985 Makovich
4,653,489 A 3/1987 Tronzo
(Continued)

FOREIGN PATENT DOCUMENTS

CA         2 560 542 A1    9/2005
DE  10 2004 011 612 A1    9/2005
(Continued)

OTHER PUBLICATIONS

European Search Report for European Application No. EP 08 01 1874.8, European Search Report dated Dec. 16, 2008 (9 pgs.).
(Continued)

*Primary Examiner* — David Bates
(74) *Attorney, Agent, or Firm* — Lewis Roca Rothgerber Christie LLP (57) ABSTRACT

A bone anchor includes a shaft having a first end and a second end, a bore extending from the first end to the second end, and a plug member which is insertable into the bore and guidable through the bore for closing the bore at the second end. The bone anchor is suitable for minimally invasive surgery in such a way a guide wire can be guided through the bone anchor and after the bone anchor has been anchored in the bone the plug member is inserted to close the open end of the bone anchor. A bone cement or a pharmaceutical substance can be introduced into the bone anchor.

11 Claims, 5 Drawing Sheets

Related U.S. Application Data continuation of application No. 12/494,107, filed on Jun. 29, 2009, now Pat. No. 8,690,930.

(60) Provisional application No. 61/077,377, filed on Jul. 1, 2008.

(52) U.S. Cl.
CPC ........ *A61B 17/864* (2013.01); *A61B 17/8685* (2013.01); *A61B 17/7032* (2013.01); *A61B 17/8897* (2013.01)

(56) References Cited

U.S. PATENT DOCUMENTS

| | | | |
|---|---|---|---|
| 4,760,843 A | 8/1988 | Fischer et al. | |
| 4,950,270 A | 8/1990 | Bowman et al. | |
| 5,047,030 A | 9/1991 | Draenert | |
| 5,129,904 A | 7/1992 | Illi | |
| 5,139,499 A | 8/1992 | Small et al. | |
| 5,169,400 A | 12/1992 | Mühling et al. | |
| 5,268,001 A | 12/1993 | Nicholson et al. | |
| 5,743,912 A | 4/1998 | Lahille et al. | |
| 5,868,749 A | 2/1999 | Reed | |
| 5,961,521 A | 10/1999 | Roger | |
| 5,968,047 A | 10/1999 | Reed | |
| 6,048,343 A | 4/2000 | Mathis et al. | |
| 6,214,012 B1 | 4/2001 | Karpman et al. | |
| 6,554,830 B1 | 4/2003 | Chappius | |
| 6,565,572 B2 | 5/2003 | Chappius | |
| 6,808,526 B1 | 10/2004 | Magerl et al. | |
| 7,074,203 B1 | 7/2006 | Johanson et al. | |
| 7,172,595 B1 | 2/2007 | Goble | |
| 7,338,493 B1 | 3/2008 | Vandewalle | |
| 7,608,097 B2 | 10/2009 | Kyle | |
| 8,579,948 B2 | 11/2013 | Biedermann et al. | |
| 2001/0007074 A1 | 7/2001 | Strobel et al. | |
| 2002/0161401 A1 | 10/2002 | Steiner | |
| 2003/0036763 A1 | 2/2003 | Bhatnagar et al. | |
| 2004/0015172 A1 | 1/2004 | Biedermann et al. | |
| 2004/0034357 A1 | 2/2004 | Beane et al. | |
| 2004/0122431 A1 | 6/2004 | Biedermann et al. | |
| 2004/0147929 A1 | 7/2004 | Biedermann et al. | |
| 2004/0195131 A1 | 10/2004 | Spolidoro | |
| 2004/0218994 A1 | 11/2004 | Boe | |
| 2004/0225292 A1 | 11/2004 | Sasso et al. | |
| 2004/0243132 A1 | 12/2004 | Whittaker | |
| 2004/0267265 A1 | 12/2004 | Kyle | |
| 2005/0096658 A1 | 5/2005 | Carchidi et al. | |
| 2005/0099015 A1 | 5/2005 | Ambs | |
| 2005/0288795 A1 | 12/2005 | Bagga et al. | |
| 2006/0011506 A1 | 1/2006 | Riley | |
| 2006/0058800 A1* | 3/2006 | Ainsworth | A61B 17/70 606/86 A |
| 2006/0100627 A1 | 5/2006 | Stone et al. | |
| 2006/0241593 A1 | 10/2006 | Sherman et al. | |
| 2006/0247642 A1 | 11/2006 | Stone et al. | |
| 2007/0016200 A1 | 1/2007 | Jackson | |
| 2007/0038219 A1 | 2/2007 | Matthis et al. | |
| 2007/0118142 A1 | 5/2007 | Krueger et al. | |
| 2007/0299450 A1 | 12/2007 | Her et al. | |
| 2008/0039846 A1 | 2/2008 | Lee et al. | |
| 2008/0132957 A1 | 6/2008 | Matthis et al. | |
| 2008/0154314 A1 | 6/2008 | McDevitt | |
| 2010/0030135 A1* | 2/2010 | Mitchell | A61M 31/00 604/48 |
| 2010/0198271 A1 | 8/2010 | Leone | |

FOREIGN PATENT DOCUMENTS

| | | |
|---|---|---|
| EP | 1 325 711 A2 | 7/2003 |
| EP | 1 825 826 A1 | 8/2007 |
| EP | 1 857 064 A1 | 11/2007 |
| EP | 1 920 722 A1 | 5/2008 |
| EP | 1 925 263 A1 | 5/2008 |
| EP | 1 938 766 A1 | 7/2008 |
| JP | 63-062968 A | 3/1988 |
| JP | 06-022671 U | 3/1994 |
| JP | 2003-159258 | 3/2003 |
| JP | 2007-307368 A | 11/2007 |
| JP | 2010-532696 A | 10/2010 |
| KR | 10-2007-0006596 A | 1/2007 |
| WO | WO 97/30649 A1 | 8/1997 |
| WO | WO 01/26568 A1 | 4/2001 |
| WO | WO 02/38054 A2 | 5/2002 |
| WO | WO 2005/007212 A2 | 1/2005 |
| WO | WO 2007/086832 A2 | 8/2007 |
| WO | WO 2009/010247 A1 | 1/2009 |

OTHER PUBLICATIONS

Office action for U.S. Appl. No. 12/821,715, dated Jan. 14, 2013, 14 pages.
Office action for U.S. Appl. No. 14/059,177, dated May 29, 2015, 8 pages.
Final Office action for U.S. Appl. No. 14/059,177, dated Oct. 23, 2015, 6 pages.
EP Office action for Application No. 13 189 297.8, dated May 29, 2015 (4 pages).
JP Office action for Application No. 2014-149741, dated May 7, 2015 (3 pages) and English translation (5 pages).

* cited by examiner

BONE ANCHOR WITH PLUG MEMBER AND TOOL FOR INSERTING THE PLUG MEMBER INTO THE BONE ANCHOR

CROSS-REFERENCE TO RELATED APPLICATIONS

This application is a continuation of U.S. patent application Ser. No. 14/188,391, filed Feb. 24, 2014, which is a continuation of U.S. patent application Ser. No. 12/494,107, filed Jun. 29, 2009, now U.S. Pat. No. 8,690,930, which claims the benefit of U.S. Provisional Patent Application Ser. No. 61/077,377, filed Jul. 1, 2008, the contents of which are hereby incorporated by reference in their entirety, and claims priority from European Patent Application EP 08 011 874.8, filed Jul. 1, 2008, the contents of which are hereby incorporated by reference in their entirety.

SUMMARY

The application relates to a bone anchor with a cannulated shaft and a plug member which is insertable into the shaft for closing the shaft at one end. The application also relates to a tool for introducing the plug member.

WO 01/26568 A1 describes a bone anchor in the form of a bone screw with a screw head and a threaded shaft which includes an axial bore and a plurality of radial bores. The axial bore is open at the screw head side and closed at the free end of the screw shaft. The known bone screw can be anchored in the bone through injecting bone cement into the shaft. This leads to a permanent and safe fixation of the bone anchor.

A bone anchor in the form of a bone screw with a cannulated shaft is also known from U.S. Pat. No. 5,047,030. The interior of the bone screw has a continuous longitudinal canal with several radially extending transverse canals which contact the longitudinal canal. The longitudinal canal is open at both ends of the screw, and it is possible to connect a vacuum pump via a tube in the area around the screw head to apply a vacuum to suck blood or other material.

WO 02/38054 A2, US 2004/0122431 A1 and US 2004/0147929 A1 disclose bone screws with a tubular threaded portion and a tip portion which can be connected to the tubular threaded portion. The tubular threaded portion has a number of recesses in its wall. It is possible to fill the tubular threaded portion with bone cement.

Minimally invasive surgery is applied in an increasing number of cases. With minimally invasive surgery in some cases guide wires are used to place an implant at the implantation site. A minimally invasive access is usually made percutaneously through the skin.

Based on the foregoing, there is a need for a bone anchor which has a broad range of application, for example which is suitable for being placed at the implantation site with minimally invasive surgery and which can be filled with a bone cement or another substance.

SUMMARY

The bone anchor according to the disclosure can be used in both, conventional surgery and minimally invasive surgery. It is possible to provide plug members for existing cannulated bone screws to render them suitable for minimally invasive surgery.

The bone anchor with the plug member prevents leaking of injected bone cement at the tip of the bone anchor. This reduces possible damages of vascular structures.

Further features and advantages will become apparent from the description of embodiments of the invention by means of the accompanying drawings.

DETAILED DESCRIPTION

FIGS. 1 to 8 show a first embodiment of a bone anchor according to the disclosure. A bone anchoring device 1 includes the bone anchor 2 for anchoring in the bone, a receiving part 3 for receiving a rod 4, a pressure element 5 acting onto the bone anchor 2 and a securing element 6. The bone anchoring device 1 according to the embodiment described is a polyaxial bone screw where the bone anchor 2 is held pivotably in the receiving part 3 which couples the bone anchor to the spinal rod 4. The angular position of the bone anchor relative to the rod can be fixed with the securing element 6.

Figure 3:
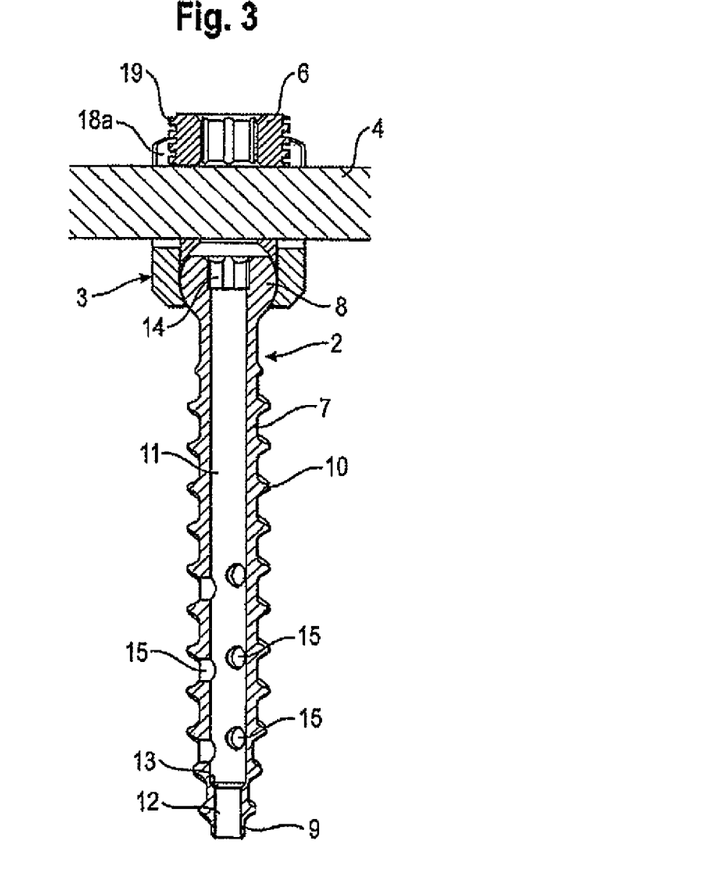
FIG. 3 shows a sectional view of the bone anchor of FIG. 2, the section being taken along a plane containing the rod axis.
Figure 4:
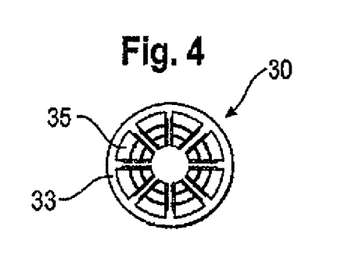
FIG. 4 shows a top view of the plug member used in the bone anchor of FIGS. 1 to 3.
Figure 5:
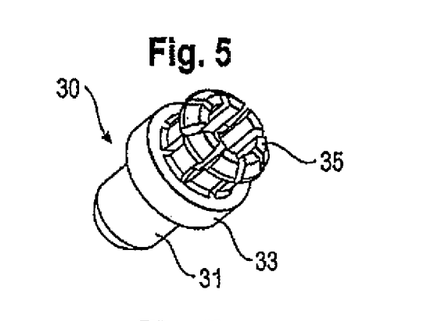
FIG. 5 shows a perspective view of the plug member of FIG. 4.
Figure 6:
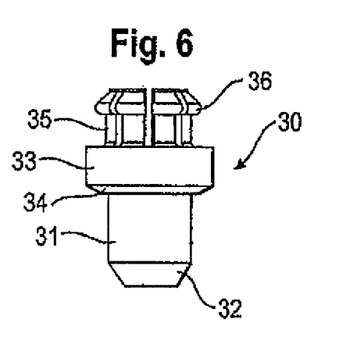
FIG. 6 shows a side view of the plug member.
Figure 7:
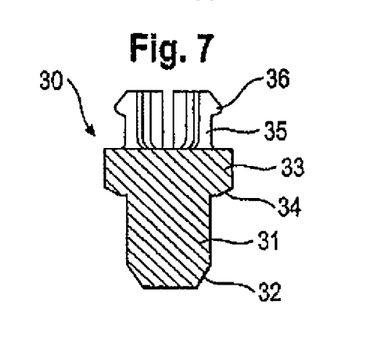
FIG. 7 shows a sectional view of the plug member.

As shown in particular in FIG. 3, the bone anchor 2 includes a shaft 7 with a head 8 at a first end and a free second end 9 which may be shaped as a tip. In the embodiment shown the head 8 has a shape of a spherical segment. Further, a bone thread 10 is provided on at least a portion of the outer surface of the shaft 7.

The bone anchor 2 is cannulated. The bone anchor 2 includes a substantially coaxial bore 11 which extends from the first end through the head 8 and the shaft 7 up to the second end 9. In a portion 12 adjacent to the second end 9 the diameter of the bore is smaller than in the main part of the shaft 7, thereby producing a shoulder 13 inside the shaft 7. At the free end of the head 8 an engagement structure 14 is provided for engagement with a tool. In the wall of the shaft 7 a plurality of openings 15 are provided which connect the bore 11 with the outside. The number, the size and the arrangement of the openings 15 is designed according to the overall dimension of the bone anchor 2 for the purpose of forming outlets for bone cement or pharmaceutical substances to be introduced into the bone anchor.

The diameter of the bore 11 and in particular of the portion 12 is designed such that a guide wire which is commonly used for minimally invasive surgery can be guided through the bone anchor 2.

Figures 1, 2:
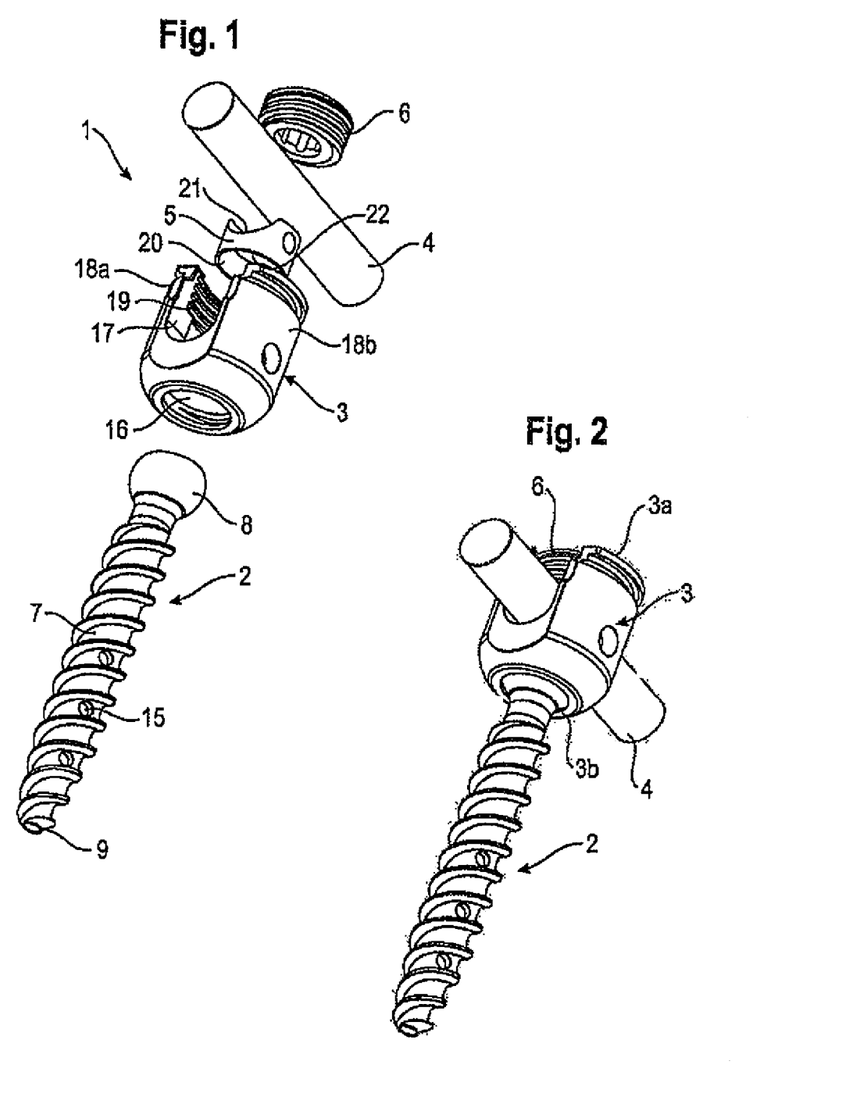
FIG. 1 shows an exploded perspective view of the bone anchor according to one embodiment.
FIG. 2 shows the bone anchor of FIG. 1 in an assembled state when the rod is fixed.

The receiving part 3 is, as shown in particular in FIGS. 1 to 3, substantially cylindrically shaped with a first end 3a and an opposite second end 3b. The receiving part 3 includes a coaxial bore 16 extending from the first end in the direction to the second end and tapering towards the second end 16 so that the head 8 of the bone anchor is pivotably held in the receiving part 3. Further, the receiving part has a substantially U-shaped recess 17 starting from the first end 3a and extending into the direction of the second end 3b by means of which two free legs 18a, 18b are formed. An internal thread 19 is provided at a portion of said free legs 18a, 18b for screwing in the securing element 6. In the embodiment, the securing element 6 is an inner screw.

The pressure element 5 serves for exerting pressure onto the head 8 of the bone anchor when the inner screw 6 is tightened so that it presses onto the rod 4. The pressure element 5 is designed such that it can be introduced into the coaxial bore 16 and moved therein in an axial direction. The pressure element 5 includes on its side facing the head 8 a substantially spherical recess 20 in order to distribute the pressure onto head 8 and on its opposite side a substantially cylindrical recess 21 for receiving the rod 4. The pressure element 5 also includes a coaxial bore 22 for guiding a guide wire or a screw tool therethrough.

As shown in FIGS. 4 to 8 the bone anchor further includes a plug member 30 for closing the bore 11 of the shaft 7 at the end portion 12 of the free second end 9. The plug member 30 is a separate part which can be introduced into the bore 11. In the embodiment shown in FIGS. 4 to 8 the plug member 30 includes a first cylindrical portion 31 the diameter of which is such that it fits into the portion 12 of the shaft 7. At the free end of the first cylindrical portion 31 a chamfered portion 32 may be provided for facilitating introduction of the plug member. Opposite to chamfered portion 32 the plug member includes a second cylindrical portion 33 the diameter of which is such that it fits to the inner diameter of the bore 11. A transitional portion 34 between the first cylindrical portion 31 and the second cylindrical portion 33 is provided which can be shaped so as to match the shape of the shoulder 13 between the main portion of the bore 11 and the end portion 12 having the reduced diameter. Hence, the shoulder 13 forms a stop for the introduction of the plug member.

At the free end of the second cylindrical portion 33 a plurality of upstanding holding springs 35 are provided. The holding springs 35 are arranged in a circle with a diameter smaller than that of the second cylindrical portion 33 and have elasticity so as to be resiliently movable outwards and/or inwards. At their free ends, the holding springs 35 comprise catches 36, respectively, for a detachable engagement with a tool described later. The holding springs 35 are arranged in such a manner that their outer portions of the catches 36 do not project outside the diameter of the second cylindrical portion 33.

Figure 8:
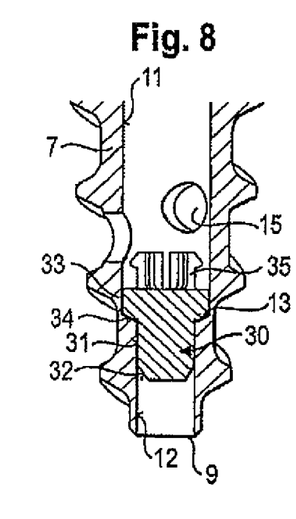
FIG. 8 shows an enlarged sectional view of the plug member of FIGS. 4 to 7 being inserted into the bone anchor.

As shown in FIG. 8, when the plug member 30 is fully inserted into the bore 11 it closes the bore at the second portion 12 so that any bone cement or pharmaceutical substance which is introduced into bore 11 cannot escape through the second end 9.

The material from which the bone anchor, the receiving part, the pressure element and the securing screw are made can be any material which is usual for these kind of devices, in particular, a body compatible metal, such as, for example, titanium or stainless steel or a metal alloy or any body compatible plastics, such as, for example, PEEK. The rod can be made of metal or plastics, depending on the application, i.e. whether the rod shall provide pure fixation or dynamic stabilisation. The material of the plug member can be the same as the material of the anchor or can be a different material. Suitable materials for the plug member are in particular titanium and titanium alloys, stainless steel used for implants and PEEK.

Figure 9:
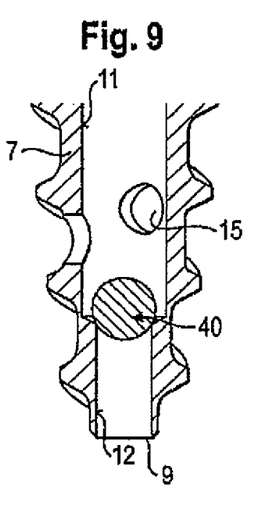
FIG. 9 shows an enlarged sectional view of a second embodiment of the bone anchor with another plug member.

A second embodiment of the plug member is shown in FIG. 9. The plug member 40 is ball-shaped with a diameter of the ball which is larger than the inner diameter of the bore 11 in the second portion 12 and smaller than the inner diameter of the bore 11 in the main portion the shaft 7. The ball-shaped plug member 40 is made advantageously of a material with a high specific weight, such as metal, so that the plug member 40 can be introduced and falls down by its own weight.

Figure 10:
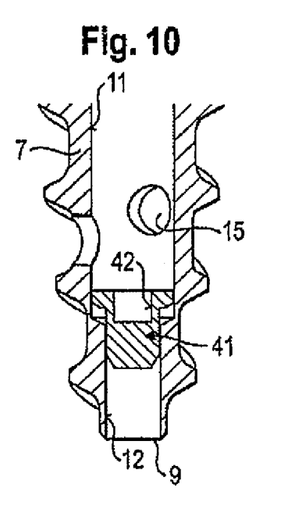
FIG. 10 shows an enlarged sectional view of a third embodiment of the bone anchor with a further plug member.

FIG. 10 shows a third embodiment of the bone anchor with a plug member 41 which differs from the plug member 30 only in that it does not have the holding springs 35 and that instead of the holding springs 35, a recess 42 is provided in the second cylindrical portion which serves for engagement with a tool. All other portions are identical to the plug member 30.

Although a polyaxial bone screw has been shown as a bone anchoring device including the bone anchor, any other bone anchor is encompassed by the disclosure. For example, a monoaxial bone screw wherein the head of the bone anchor 2 is shaped so as to receive the rod can be used. The bone anchor further does not need to have a bone thread provided on the shaft. It can also be designed as a push and turn anchor having barb elements for retention in the bone. The bone anchor also can be designed as a bone nail with smooth outer surface.

Other modifications of the plug member are also conceivable. For example, the plug member can be disk-shaped, cone-shaped or can have any other shape.

Figures 11, 13:
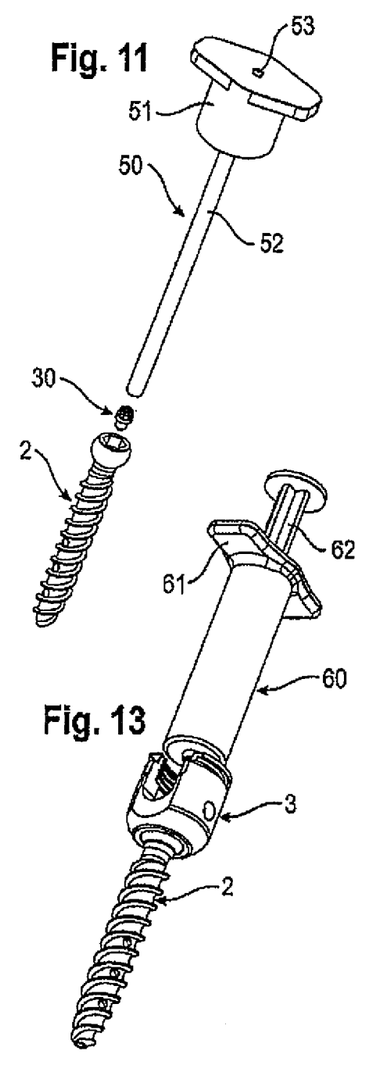
FIG. 11 shows an exploded view of a first embodiment of a tool for inserting the plug member into the bone anchor.
FIG. 13 shows a perspective view of the bone anchor with a second embodiment of a tool in a position of injecting bone cement.
Figures 12, 14:
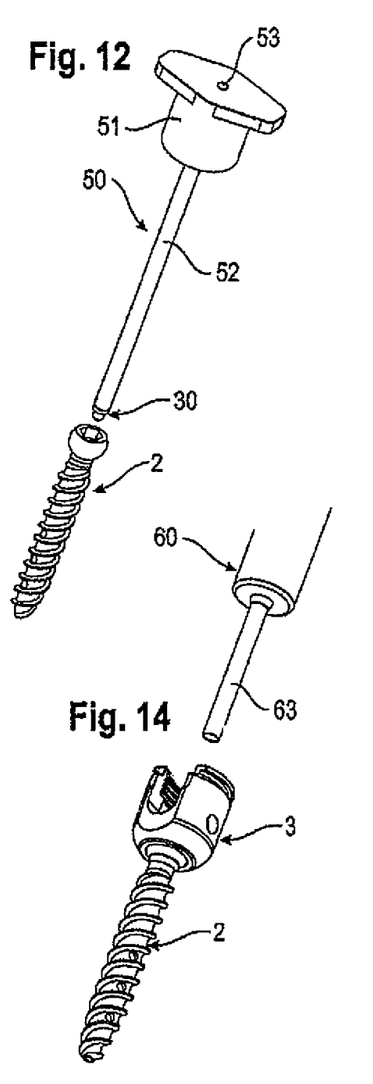
FIG. 12 shows a perspective view of the bone anchor with the tool of FIG. 11 assembled with the plug member.
FIG. 14 shows the bone anchor with the second embodiment of the tool in an exploded view.

A first embodiment of a tool for inserting the plug member into the bone anchor is now described with reference to FIGS. 11 and 12. The tool 50 is particularly suitable for inserting the plug member of the type shown in FIGS. 4 to 8. The tool 50 includes a handle 51 for gripping and an insertion tube 52 extending through the handle 51. The insertion tube 52 is hollow and has a length which is at least as long as the length of the shaft so as to be able to position the plug member 30 at the end of the bore 11. The inner diameter of the tube 52 is such that the tube 52 can be placed onto the holdings 35 of the plug member so that the holding springs with the catches 36 are moved inwards to a certain extent. In this manner they are gripped at the end of the tube 52. The insertion tube 52 may have at its end inside a recess cooperating with the catches 36. The outer diameter of the tube 52 is slightly smaller than the inner diameter of the bore 11, so that the insertion tube 52 can be introduced into bore 11. The insertion tube 52 extends through the handle 51 so that the open end 53 of the tube 52 is substantially flush with the end portion of the handle 51. FIG. 11 shows the anchor 2, the plug member 30 and the tool 50 in an exploded view. In the representation of FIG. 12 the plug member 30 is gripped by the tool 50. Since the tube 52 extends through the handle 51 it is possible to guide a guide wire through the open end 53 into the tube portion.

FIGS. 13 and 14 show two positions of a second embodiment of the tool with respect to the bone anchor.

The tool 60 according to this embodiment is formed by a syringe 60. The syringe 60 is particularly suitable for injection of bone cement or pharmaceutical substances into the bone anchor 2. The syringe 60 includes a barrel with a handle 61 for gripping and a plunger 62 for pushing the bone cement or the substance into a needle or tube 63. The needle or tube 63 is designed so as to be able to grip the plug member 30 or to engage into the recess 42 of the plug member 41. The needle or tube 63 is long enough so that the plug member can be placed at the end of the bore 11.

Modifications of these tools are also conceivable. For example, the insertion tubes 52 or 63 can be flexible so as to be adaptable to non-straight channels in the bone anchor. Any other gripping mechanism with, for example, release function for gripping and releasing the plug member is possible.

Figure 15:
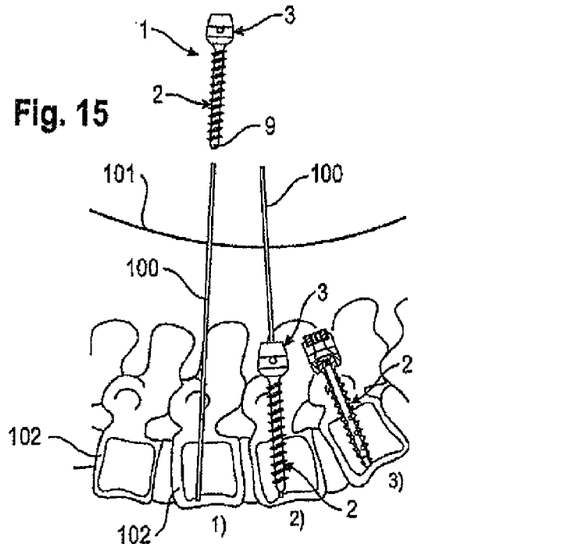
FIG. 15 shows steps of using the bone anchor in minimally invasive surgery.
Figure 16A:
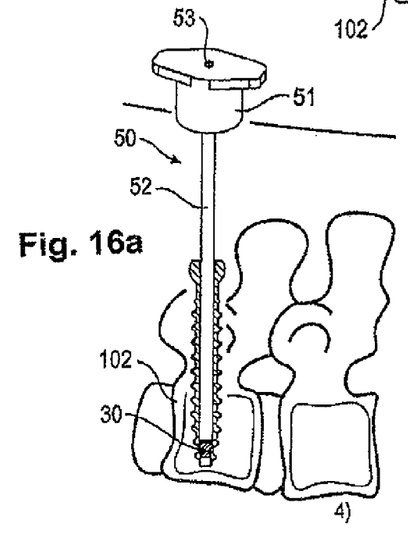
FIGS. 16a- to 16c show steps of using the bone anchor in minimally invasive surgery.
Figures 16B, 16C:
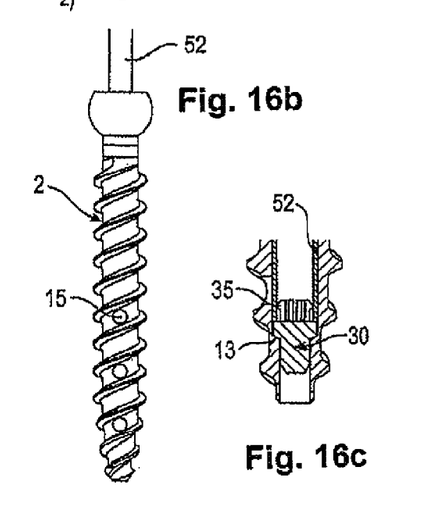

Use of the bone anchor is now described with respect to FIGS. 15 and 16. FIGS. 15 and 16 show the implantation of the bone anchor with minimally invasive surgery. In a first step, a guide wire 100 is placed percutaneously through the skin 101 to the final position of the bone anchor in a vertebra 102 of the vertebral column. The plug member is not inserted into the bone anchor as this stage of the procedure. Thereafter, the bone anchor 2 or, as shown in FIG. 15, the bone anchor preassembled with the receiving part 3 and the pressure element 5 is provided and the guide wire 100 is guided through the bone anchor and the receiving part 3 from the first end 9 of the bone anchor. Next, the bone anchoring device 1 is guided along the guide wire 100 to the vertebra 102 which is the final implantation site and is finally, screwed into the pedicle. Thereafter, the guide wire is removed.

FIGS. 16a to 16c show the steps of introducing the plug member. As shown in FIG. 16a, the tool 50 is used to introduce the plug member 30 into the bone anchor 2. FIG. 16b shows a side view and FIG. 16c a sectional view of an enlarged portion of the anchor 2 with the plug member 30 inserted by the tube 52. The plug member 30 is gripped by the tube 52 of the tool 50 and the tube 52 is introduced into the bone anchor. The plug member 30 is then detached from the tool by inserting the guide wire 100 (not shown) and pushing the guide wire 100 against the plug member so that the plug member finally rests on the shoulder 13 and closes the bone anchor. Thereafter, bone cement or a pharmaceutical substance is injected which exits through the openings 15 into the surrounding bone material. It cannot exit through the free end 9 of the bone anchor since the free end 9 is closed by the plug member. This results in a safe fixation, since there is no leakage of bone cement at the free end 9 which could loosen the anchor or damage vascular structures.

In case of the plug member 40 which is ball-shaped, the plug member 40 is only introduced into the upper portion of the bore 11 so that it falls down by its own weight and closes the free end 9.

In an alternative manner the plug member 30 or 41 is gripped by the needle 63 of the syringe 60 containing the bone cement or the pharmaceutical substance and the plug member is injected through injection of the bone cement or the pharmaceutical substance into bore 11 until it closes the free end.

After at least two bone anchors are anchored, the rod 4 is inserted and fixed by means of the securing element.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchor, comprising:
a monolithic tubular shaft defining a bore having a first open end and a second open end opposite to the first open end along a longitudinal axis of the shaft, the shaft including a plurality of openings through a tubular wall of the shaft and spaced apart from the first open end; and
a plug member configured to be implanted into a bone with the tubular shaft, wherein the plug member is configured to be inserted into the bore from the first open end and guidable through the bore past at least one of the openings to a first position along the longitudinal axis for closing the bore between the first open end and the second open end while a pathway between the first open end and the at least one of the openings remains open;
wherein a first section of the plug member has a different cross-section from a second section of the plug member, such that when the plug member is at the first position, the first section of the plug member abuts a shoulder formed in the bore of the tubular shaft to prevent further movement of the plug member towards the second open end, and the second section of the plug member restricts tilting of the plug member relative to the tubular shaft.

2. The bone anchor of claim 1, wherein a cross section of the bore near the second open end is different than a cross section of the bore at the first open end to form the shoulder, the shoulder defining a stop, and wherein when the plug member is at the first position, the second section of the plug member is inserted through the bore past the stop, while the first section of the plug member engages the stop to limit further insertion of the plug member through the bore.

3. The bone anchor of claim 1, wherein the bore is configured to accommodate a guide wire therein for minimally invasive surgery.

4. The bone anchor of claim 1, wherein the plug member is substantially pin-shaped.

5. The bone anchor of claim 1, wherein the plug member comprises an engagement structure for engagement with a tool.

6. The bone anchor of claim 5, wherein the engagement structure comprises a recess.

7. The bone anchor of claim 1, wherein the first end comprises a head.

8. The bone anchor of claim 7, wherein the head is configured to be connected to a receiving part for receiving a rod.

9. A bone anchor, comprising:
a tubular shaft defining a bore having a first open end and a second open end opposite to the first open end along a longitudinal axis of the shaft, the shaft including a plurality of openings through a tubular wall of the shaft and spaced apart from the first open end;
a plug member configured to be implanted into a bone with the tubular shaft, wherein the plug member is configured to be inserted into the bore from the first open end and guidable through the bore past at least one of the openings along the longitudinal axis for closing the bore between the first open end and the second open end;

wherein the plug member comprises a first portion having a greatest width of the plug member, a second portion projecting from the first portion and having a width that is less than the width of the first portion, and an engagement structure for engagement with a tool that projects from a side of the first portion opposite the second portion and having a width that is less than the width of the first portion.

10. The bone anchor of claim 9, wherein the engagement structure comprises a recess.

11. A bone anchor comprising:

a tubular shaft defining a bore extending from a first open end to a second open end opposite to the first open end along a longitudinal axis of the shaft, the bore having a first portion and a second portion at the second open end, wherein the first portion has a greater inner diameter than an inner diameter of the second portion, wherein a shoulder is formed in the shaft between the first portion and the second portion, and wherein a plurality of openings that are spaced apart from the first open end extend through a tubular wall of the shaft;

a plug member configured to be implanted into a bone with the tubular shaft, the plug member having a first portion and a second portion, wherein an outer diameter of the first portion is greater than an outer diameter of the second portion, forming a recessed transition portion between the first and second portions of the plug member;

wherein the plug member is moveable from a first position inside the bore at the first open end to a second position past at least one of the openings along the longitudinal axis to close the bore while a pathway between the first open end and the at least one of the openings remains open; and wherein the outer diameter of the first portion of the plug member is greater than the inner diameter of the second portion of the bore, such that when the plug member is at the second position, the plug member abuts the shoulder of the tubular shaft and the first portion of the plug member is prevented from entering the second portion of the bore.

* * * * *